US008091765B2

(12) United States Patent
Jiang et al.

(10) Patent No.: US 8,091,765 B2
(45) Date of Patent: *Jan. 10, 2012

(54) METHOD OF BONDING TITANIUM TO STAINLESS STEEL

(75) Inventors: Guangqiang Jiang, Santa Clarita, CA (US); Atilla Antalfy, Castaic, CA (US)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 1161 days.

This patent is subject to a terminal disclaimer.

(21) Appl. No.: 11/336,596

(22) Filed: Jan. 20, 2006

(65) Prior Publication Data

US 2006/0113357 A1 Jun. 1, 2006

Related U.S. Application Data

(62) Division of application No. 10/821,023, filed on Apr. 7, 2004, now abandoned.

(51) Int. Cl.
*B23K 1/20* (2006.01)
(52) U.S. Cl. ........................................................ 228/203
(58) Field of Classification Search .................. 228/203, 228/245, 246, 248.1, 253, 56.3; 428/661, 428/648, 680, 685
See application file for complete search history.

(56) References Cited

U.S. PATENT DOCUMENTS

| | | | | |
|---|---|---|---|---|
| 3,994,430 A * | 11/1976 | Cusano et al. | ............. | 228/122.1 |
| 4,433,230 A * | 2/1984 | Sano et al. | ..................... | 219/118 |
| 6,109,339 A * | 8/2000 | Talbert et al. | ................ | 165/48.1 |
| 6,521,350 B2 * | 2/2003 | Fey et al. | ....................... | 428/472 |
| 6,722,002 B1 * | 4/2004 | Chang et al. | ................... | 29/17.2 |
| 6,875,949 B2 * | 4/2005 | Hall | ........................ | 219/121.64 |
| 7,201,973 B2 * | 4/2007 | Pohlman et al. | ............. | 428/661 |
| 2004/0105999 A1 * | 6/2004 | Abkowitz et al. | ............. | 428/660 |

* cited by examiner

*Primary Examiner* — Jessica L Ward
*Assistant Examiner* — Steven Ha
(74) *Attorney, Agent, or Firm* — Gary D. Schnittgrund

(57) ABSTRACT

A method of bonding a stainless steel part to a titanium part by heating a component assembly comprised of the titanium part, the stainless steel part, and a laminated titanium-nickel filler material placed between the two parts and heated at a temperature that is less than the melting point of either the stainless steel part or the titanium part. The component assembly is held in intimate contact at temperature in a non-reactive atmosphere for a sufficient time to develop a hermetic and strong bond between the stainless steel part and the titanium part. The bonded component assembly is optionally treated with acid to remove any residual free nickel and nickel salts, to assure a biocompatible component assembly, if implanted in living tissue.

11 Claims, 3 Drawing Sheets

METHOD OF BONDING TITANIUM TO STAINLESS STEEL

CROSS REFERENCE TO RELATED APPLICATION

This application is a divisional of U.S. patent application Ser. No. 10/821,023, filed Apr. 7, 2004.

DETAILED DESCRIPTION OF THE PREFERRED EMBODIMENT

Figure 1:
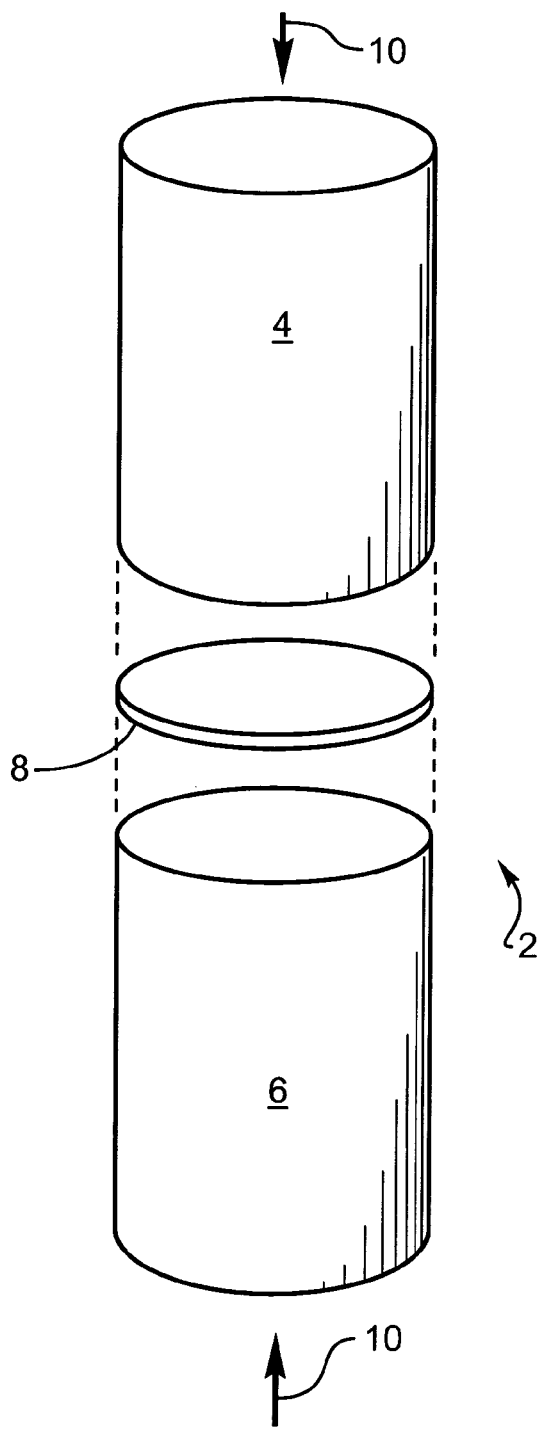
FIG. 1 illustrates a side view of the component assembly with filler material as a foil between the stainless steel part and the titanium part.

FIG. 1 presents component assembly 2 having a titanium part 4, a stainless steel part 6, and a filler material 8. Component assembly 2 is heated to a specific process temperature that is below the melting point of titanium part 4 or of the melting point of stainless steel part 6, for a specific period of time, at a pressure that is created by force 10, that is exerted to place filler material 8 in intimate contact with the titanium part 4 and stainless steel part 6.

Figure 3:
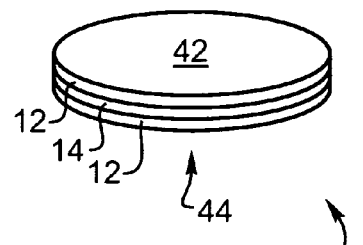
FIG. 3 presents an isometric view of a titanium-nickel laminated filler material having three foil layers.

Filler material 8 is preferably a laminate metal foil having a thickness of approximately ten-thousandths (0.010) of an inch and more preferably less than 0.010 inches. Filler material 8 is selected from the group of materials that are compatible with the stainless steel chosen for stainless steel part 6 in that they wet the surface during the bonding process and enter into a diffusion process with the stainless steel part 6, thereby creating a strong bond joint during processing. Filler material 8 is further selected from the group of materials that are compatible with the titanium part 4. Filler material 8 forms a bond between titanium part 4 and stainless steel part 6 at the bonding temperature and pressure utilized during processing. The group of filler materials that are compatible with both the stainless steel part 6 and the titanium part 4 includes substantially pure titanium and nickel laminate compositions, preferably comprised of filler materials of about 22% to 98% nickel and the balance titanium. In a preferred embodiment, FIG. 3, filler material 8 is preferably comprised of alternating foil layers 12 and 14. Preferably, for example, as shown in FIG. 3, a laminate stack of commercially pure nickel layer 12 on the top outer surface 42 and a similar nickel layer 12 on the bottom outer surface 44. Sandwiched between the nickel layers 12 is a titanium layer 14. The nickel layer 12 having at least 99.0% nickel and less than 1.0% of other elements with a thickness of greater than approximately 0.0003 inches and the titanium layer 14 comprised of commercially pure titanium foil having at least 99.0% titanium and less than 1.0% of other elements with a thickness of greater than approximately 0.0003 inches.

The inventors prefer the term "laminated" versus other descriptive, but equally applicable, terms such as "layered", "clad", or "composite" material. The laminated filler material is not an "alloy" of nickel and titanium. An alloy, which is defined as a homogeneous mixture of two or more metals, where the atoms of one replace or occupy interstitial positions between the atoms of the other, of nickel and titanium, for example, does not demonstrate the depressed melting point that is available at a eutectic composition when nickel and titanium are in intimate contact. The laminate material supplies substantially pure nickel to initiate bonding with other metals, such as titanium or stainless steel, for example, at relatively low eutectic temperatures. For example, the lowest liquidus temperature (also referred to herein as the melting point) in the nickel-titanium phase diagram occurs at 28% by weight nickel and is 942° C. Therefore, the optimum braze temperature will be greater than this temperature.

Figure 4:
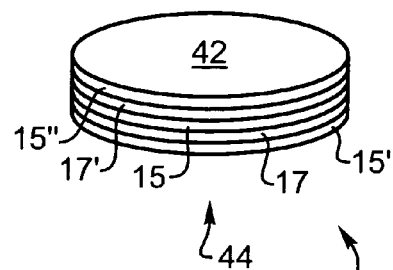
FIG. 4 presents an isometric view of a titanium-nickel laminated filler material having five foil layers.

In a further preferred embodiment, FIG. 4, the metal foil layers 15, 15', and 15", which are comprised of nickel, are placed in laminated filler material 8 as the top outer surface 42 and as the bottom outer surface 44, thereby making the nickel available to react directly with the stainless steel part 6 and the titanium part 4. Alternating layers of inner mating foil layer 17 and 17', which are comprised of titanium, are placed between the metal foil layers 15, 15', and 15".

Those skilled in the art know that the total composition of a laminate stack of alternating nickel and titanium foil is controlled by the thickness of the foil layers, where the volume fraction of nickel and titanium is converted to weight percent by accounting for the density of the nickel and titanium. For example, to achieve a total laminate stack composition of a filler material 8 having a composition of 50 weight percent Ni and 50 weight percent Ti, where the density of nickel is 8.90 g/cc and of titanium is 4.51 g/cc, the thickness of the filler material 8 will be 33.6% Ni foil and 66.4% Ti foil.

Titanium part 4 may be comprised of a titanium alloy and is comprised of Ti-6Al-4V, i.e. an alloy of titanium with 6 weight percent aluminum and 4 weight percent vanadium, in a preferred embodiment. Stainless steel part 6 may be comprised of one of the corrosion resistant stainless steels, such as, 304 stainless steel, or a 200, 300, or 400 series stainless steel, and in a preferred embodiment stainless steel part 6 is comprised of 316L stainless steel. This configuration of components offers the advantage of being biocompatible and of being capable of forming hermetic seals.

In an alternate embodiment, rather than using filler material 8 as a foil, filler material 8 may be a thin coating that is applied to the bonding surface of either the titanium part 4 or stainless steel part 6 by any of a variety of chemical processes, such as electroless plating and electroplating, or by any of a variety of thermal processes, such as sputtering, evaporating, or ion beam enhanced deposition.

In another embodiment, filler material 8 is applied as a thin coating of metallic beads, metallic powder, or discrete particles. The coating may be applied in any of several methods known to those skilled in the art, such as painting, spraying, or dipping. The applied coating consists of discrete particles of nickel and of titanium that aid in bonding the stainless steel part 6 and the titanium part 4 during the braze process.

Figure 5:
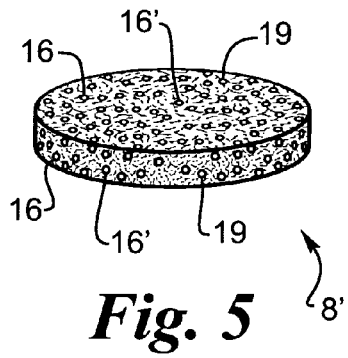
FIG. 5 illustrates the compact filler material comprised of discrete particles of titanium and nickel.

In a further alternate embodiment, a compact filler material 8', FIG. 5, is comprised of a bonded compact of primary alloy particulate 16 and secondary alloy particulate 16', where primary alloy particulate 16 is preferably comprised of a nickel alloy and primary alloy particulate 16' is preferably comprised of a titanium alloy. The compact filler material 8' is formed by any of several techniques that are known to one skilled in the art, including cold pressing, warm pressing, slurry preparation, etc. The intimate mixture of primary alloy particulate 16 and secondary alloy particulate 16' bond together as well as react with the stainless steel part 6 and the titanium part 4 during the braze operation to yield a bonded component assembly 2.

Figure 6:
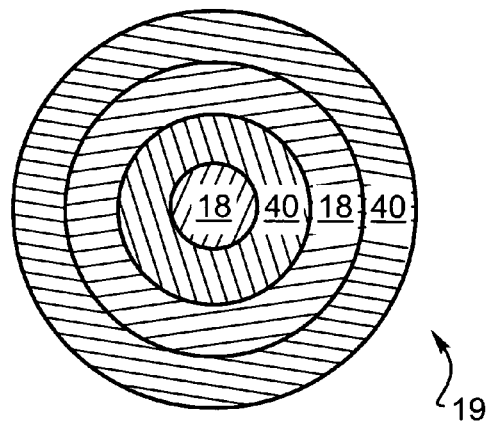
FIG. 6 presents a cross-sectional view of a discrete particle of nickel and titanium layers.

Yet another alternate embodiment of forming a bonded component assembly 2 utilizes the compact filler material 8', as presented in FIG. 5, that is comprised of layered discrete particle 19, preferably spheres, comprised of layered or laminated composition, as shown in FIG. 6. In a preferred embodiment, layered discrete particle 19 is comprised of alternating layers of primary particle laminate layer 18 and secondary particle laminate layer 40, where primary particle laminate layer 18 is preferably comprised of nickel and secondary particle laminate layer 40 is comprised of titanium. The overall bonding methods and processes are analogous to those employed for the several embodiments.

Figure 2:
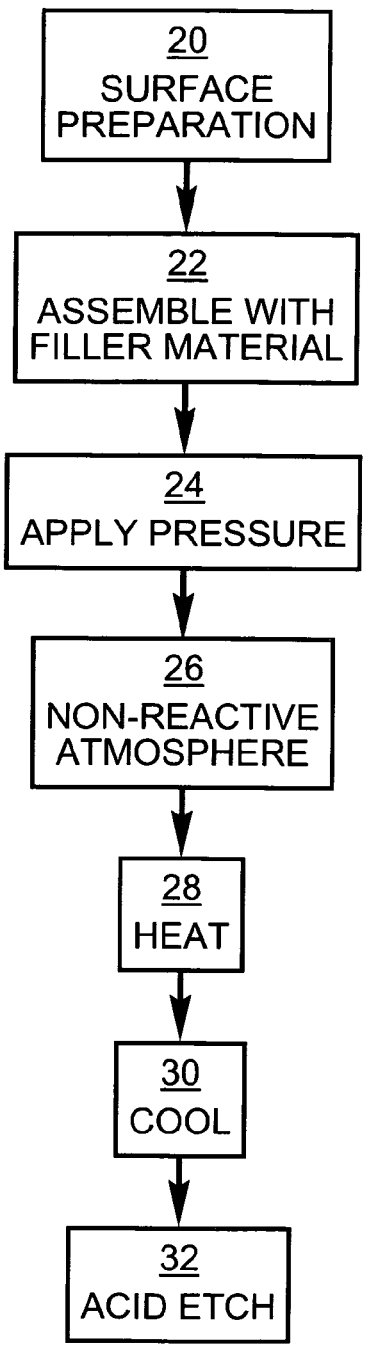
FIG. 2 schematically depicts the bonding steps of the present invention.

The process steps that are employed to create component assembly 2 with a strong bond between titanium part 4 and stainless steel part 6 are schematically represented in FIG. 2. First, the surfaces to be bonded are prepared in step 20 by machining to assure that they will intimately conform to each other during bonding. The surfaces are smoothed and cleaned.

In step 22, component assembly 2 is prepared with filler material 8 between titanium part 4 and stainless steel part 6. In step 24, force 10 is applied to compress filler material 8 between titanium part 4 and stainless steel part 6. Force 10 is sufficient to create intimate contact between the parts. Force 10 is applied to assure that a bond is formed between titanium part 4 and stainless steel part 6, thus creating a hermetic seal between the two parts. It is preferred that the resulting pressure be greater than about five psi.

In step 26, the assembly to be heat processed is placed in a furnace in a non-reactive atmosphere, which is preferably vacuum, but which, in an alternative embodiment, can be any of several atmospheres that are known to those skilled in the art, such as argon, nitrogen or hydrogen. A non-reactive atmosphere is applied before the furnace is heated to the processing temperature in step 28. A preliminary holding temperature may be utilized to allow the thermal mass of the parts to achieve equilibrium before proceeding with heating. In a preferred embodiment, the vacuum is less than $10^{-5}$ torr, to assure that the filler material 8 and titanium part 4 do not oxidize. Component assembly 2 is held at the selected temperature, which is between approximately 940° and 1260° C., for approximately 5 to 60 minutes, while force 10 continues to be exerted on filler material 8. The exact time, temperature and pressure are variable with each other so as to achieve a strong bond between titanium part 4 and stainless steel part 6. For example, in a preferred embodiment, a 316L stainless steel part is bonded to a Ti-6Al-4V part in vacuum at $10^{-6}$ torr at approximately 1000° C. for 10 minutes with a pressure of about 50 psi on a nickel-titanium foil of approximately 0.002 inches total thickness.

The furnace is cooled and component assembly 2 is cooled to room temperature in step 30. In optional step 32, component assembly 2 is cleaned by being placed in a bath, after thermal processing is complete, to assure removal of all nickel and nickel salts. This bath is preferably an acid bath that etches the exposed surfaces of component assembly 2. In a preferred embodiment, the bath is nitric acid. Removal of nickel and nickel salts in the etch bath insures that component assembly 2 is biocompatible. Nickel and nickel salts are detrimental to living animal tissue. It is preferred that all of the nickel that is introduced as filler material 8 is combined with the titanium and is chemically tied up by thermal processing to be unavailable as free nickel or as a nickel salt. Component assembly 2 is biocompatible after bonding and processing.

Figure 7:
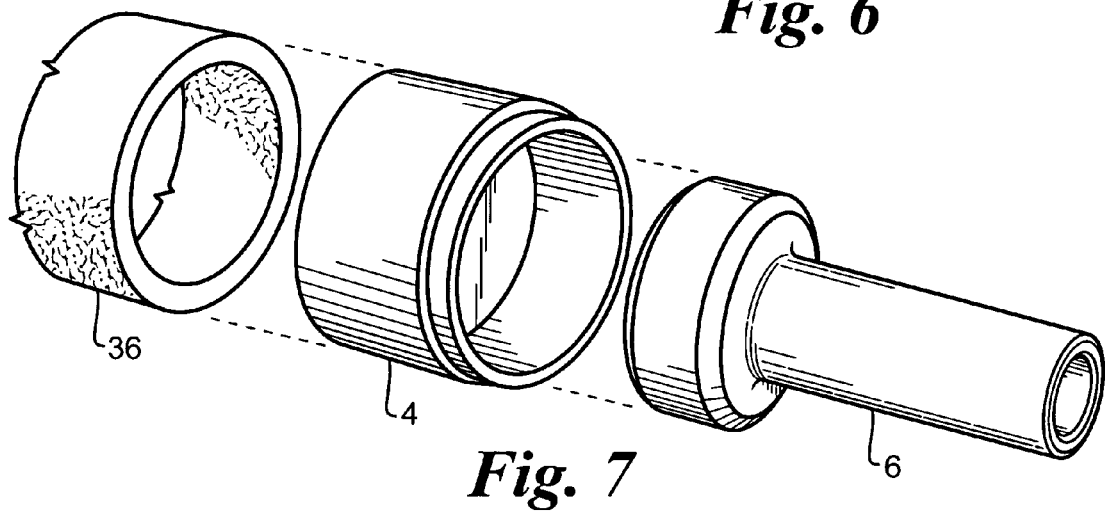
FIG. 7 presents an exploded isometric view of a ceramic tube, titanium part, and stainless part.

In a preferred embodiment, component assembly 2 is either an electrical sensor or an electrical stimulator that is implanted in a human body, although it could equally well be implanted in any animal. It must survive long periods in the hostile environment of a living body, which is basically a warm saline solution. In a preferred embodiment, component assembly 2 is either a sensor or stimulator comprised of a hollow ceramic tube 36, containing various electronic components, that is bonded to a titanium electrode end. The component assembly must be watertight, resisting salt-water intrusion as well as growth of living tissue into the titanium-to-stainless steel braze joint. FIG. 7 presents an exploded isometric view of a ceramic tube 36 that is bonded to a titanium part 4 and a stainless steel part 6. The stainless steel part 6 is designed to accept an electrically conductive wire, for transmission of electrical signals.

Further, component assembly 2 does not corrode while implanted in the body. The materials are chosen such that post-bonding they are not susceptible to corrosion either individually or in the as-bonded state. Component assembly 2 resists electrolytic corrosion as well as crevice corrosion, because of the materials selected for construction of component assembly 2.

Figure 8:
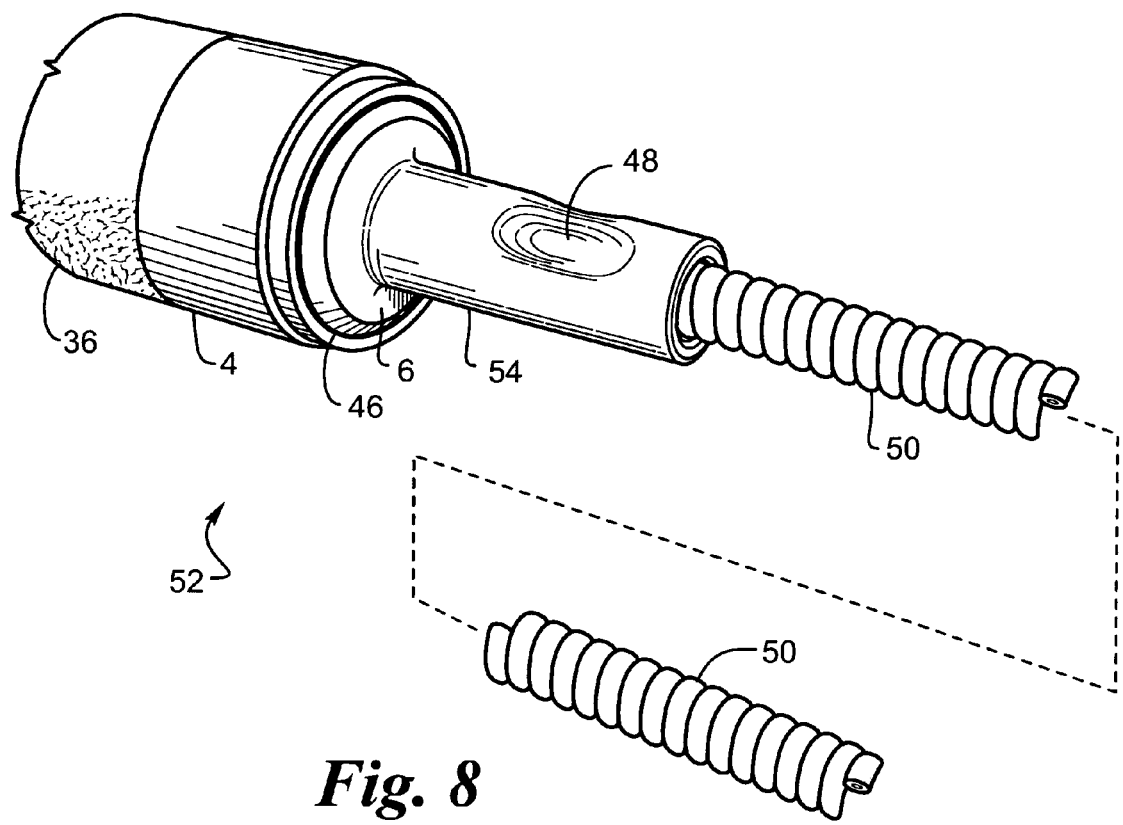
FIG. 8 illustrates a bonded device with a crimp-attached wire.

A bonded device 52 is presented in FIG. 8 wherein a ceramic tube is bonded to titanium part 4 which is bonded to stainless steel part 6 with a filler material at braze joint 46. Stainless steel part 6 contains a receiver 54 into which a wire 50 is inserted and attached, preferably by crimping, such that crimp indentation 48 retains wire 50. The bonded device 52 provides good electrical conductivity via stainless steel part 6 connecting to wire 50. Stainless steel part 6 is brazed to titanium part 4 that is bonded by known methods to ceramic tube 36.

Obviously, many modifications and variations of the present invention are possible in light of the above teachings. It is therefore to be understood that, within the scope of the appended claims, the invention may be practiced otherwise than as specifically described.

What is claimed is:

1. A method of making a living tissue implantable component assembly, comprising the steps of:

selecting a biocompatible 316L stainless steel part;

selecting a biocompatible titanium part that is comprised of Ti-6Al-4V;

selecting a laminated filler material that is less than about 0.010 inches thick that is comprised of a 22% to 98% nickel portion and a remaining titanium portion, said laminated filler material comprising at least two nickel layers surrounding at least one titanium layer, selecting said laminated filler material having a melting point that is lower than the melting point of said titanium part and said stainless steel part;

positioning said filler material between said stainless steel part and said titanium part;

placing the assembly in a non-reactive atmosphere;

applying a force to said stainless steel part and said titanium part to place said filler material in compression, thereby creating intimate contact between said stainless steel part, said filler material, and said titanium part;

heating the assembly to a temperature between said melting point of said laminated filler material and said melting point of said titanium part;

holding the assembly at said bonding temperature for a predetermined time to form a bond between said stainless steel part and said titanium part;

cooling the assembly; and implanting the component assembly in a human body.

2. The method of claim 1 wherein said step of applying a force creates compression between about 5 and 50 psi.

3. The method of claim 1 wherein said step of applying a force creates compression between about 5 and 7 psi.

4. The method of claim 1 further comprising the step of forming said filler material from metallic particulate.

5. The method of claim 1 further comprising the step of placing the assembly in a non-reactive atmosphere is placing in a vacuum less than $10^{-5}$ Torr.

6. The method of claim 1 further comprising the step of placing the assembly in a non-reactive atmosphere is placing in argon gas.

7. The method of claim 1 wherein said bonding temperature is between approximately 940° and 1260° C.

8. The method of claim 1 wherein said predetermined time is between approximately 5 and 60 minutes.

9. The method of claim 1 additionally comprising the step of cleaning said component assembly after bonding to remove elemental nickel and nickel salts.

10. The method of claim 9 additionally comprising the step of cleaning said component assembly after bonding by placing it in an acid bath.

11. A method of making a living tissue implantable component assembly, comprising the steps of:

selecting a biocompatible stainless steel part from the group consisting of corrosion resistant stainless steels;

selecting a biocompatible titanium part comprised of Ti-6Al-4V;

positioning a laminated filler material between said stainless steel part and said titanium part;

applying a force to said stainless steel part and said titanium part to place said filler material in compression between 5 and 7 psi, thereby forming said component assembly;

placing said component assembly in a non-reactive atmosphere;

heating said component assembly to between approximately 940° and 1260° C. for between approximately 5 and 60 minutes;

cooling said component assembly;

cleaning said component assembly after cooling to remove elemental nickel and nickel salts; and implanting the component assembly into a human body.

* * * * *